United States Patent [19]

Mooth

[11] 4,155,888

[45] May 22, 1979

[54] WATER-ABSORBENT STARCHES

[75] Inventor: Robert A. Mooth, Decatur, Ill.

[73] Assignee: A. E. Staley Manufacturing Company, Decatur, Ill.

[21] Appl. No.: 897,227

[22] Filed: Apr. 17, 1978

[51] Int. Cl.$^2$ .............................................. C08L 3/02
[52] U.S. Cl. ...................... 260/17.4 GC; 260/17.4 ST
[58] Field of Search ................................ 260/17.4 GC

[56] References Cited

U.S. PATENT DOCUMENTS

| | | | |
|---|---|---|---|
| 2,668,156 | 2/1954 | Caldwell et al. | 260/17.4 UC |
| 3,976,552 | 8/1976 | Fanta et al. | 260/17.4 ST |

*Primary Examiner*—Edward M. Woodberry

*Attorney, Agent, or Firm*—M. Paul Hendrickson; Charles J. Meyerson

[57] ABSTRACT

Water-absorbent starch products may be prepared by simultaneously drying and polymerizing an aqueous media containing starch, ethylenic unsaturated monomer and free-radical initiator. Without necessitating further refining or chemical modification, effective water-absorbent, drum-dried products essentially free from water-soluble salts and free-radical initiator contaminants and containing a high level of functional water-attractant groups may be directly manufactured. If desired, the water-absorbent starch products may be further refined to increase the water-absorbent properties of the starch polymer.

14 Claims, No Drawings

WATER-ABSORBENT STARCHES

This invention relates to water-absorbent starch products, the manufacture thereof and the use of the water-absorbent starch products.

BACKGROUND OF THE INVENTION

Within recent years, considerable interest has existed in starch derivatives which are capable of absorbing and retaining large amounts of water. Water-absorbent starches developed at U.S.D.A. Laboratories (e.g., see U.S. Pat. Nos. 3,935,099; 3,997,484; 3,985,616; 3,981,100 and 4,405,387) reportedly absorb more than 1,000 times their dry weight in water. These water-absorbent starches are prepared by grafting polyacrylonitrile to starch molecules in a confined polymerization reactor and thereafter chemically derivatizing the nitriles to carboxyamides and carboxylates. Grafting is typically accomplished by free-radical initiation with ceric ions which remain as a residual contaminant even though the product may be extensively refined. The grafting level is critical, difficult to control and time-consuming.

After the polyacrylonitrile-starch copolymer has been formed, the nitrile groups are saponified to the water-absorbent starch product. The saponification is preferably accomplished by reacting the nitrile groups with an alkaline hydroxide to form carboxylate and carboxyamide groups respectively at a molar ratio of about 2:1. The 66% carboxylate and 33% carboxyamide ratio remains relatively constant. Distribution and sequence of the carboxylate and carboxyamide groups throughout the graft portion follows a regular pattern. Residual heterocyclic nitrogen contaminants (an intermediate reaction product) may be carried into the final product. The water-absorbency properties of the saponified product is significantly improved by purifying the product. Notwithstanding, salt contaminants (as well as the initiators) are difficult to remove and can interfer with the overall water absorbing characteristics of the finished product.

In U.S. Pat. No. 3,640,925 by Touzinsky et al., a process for producing starch graft copolymers is disclosed. In this process, a conventional starch jet cooker operated at superatmospheric pressures and elevated temperatures is used as a copolymerization reactor. An aqueous slurry containing up to 43% by weight starch, comonomer in an amount up to 37% by weight of the starch and free-radical initiator is passed through the starch cooker, rapidly heated to 190°-340° F. to instantaneously paste the starch and to simultaneously initiate the graft copolymerization between the pasted starch and the monomers. After the copolymerization reaction has been completed, the graft copolymerizate may be converted to a dry product. Reportedly a wide variety of acrylic and vinyl monomers may be grafted by this procedure. The need to purify or blanket the copolymerization reactor with nitrogen or exclude air or oxygen (deemed essential to the grafting process) is reportedly avoided. The starch graft copolymers are reportedly useful as wet-end paper and textile sizes. Touzinsky et al. do not contemplate water-absorbent starch products.

British Pat. No. 1,495,845 reports starch and synthetic polymer aqueous mixtures may be roll-dried at elevated temperatures to provide graft polymers which may be used as thickening agents in latices and adhesive dispersions.

A simple and more economical process for producing water-absorbent starch products would represent a significant advance towards the commercial adaptation of these potentially useful products. A process which would eliminate the need for copolymerization and saponification reactors would have a decided advantage over the most highly regarded processes. It also would be a decided commercial advantage to conduct the process in such a manner so as to avoid contamination of the water-absorbent starch products with initiator and saponification salt residues. Greater versatility with respect to the types of monomers copolymerized with the starch and the ability to introduce a predetermined and/or higher level of water-attractant moieties into the synthetic copolymer portion would afford the art the ability to manufacture uniquely different water-absorbent starch products.

OBJECTS

An object of the invention is to provide a simple and more economical method for manufacturing water-absorbent starch products.

Another object is to provide novel water-absorbent starch products.

A still further object is to eliminate transitional or heavy metal initiators, saponification reactants and reaction product contaminants from the water-absorbent starch products.

An additional object is to increase the level of water-attractant copolymerized ethylenically unsaturated monomer groups in the synthetic polymer portion of the water-absorbent starch product.

THE INVENTION

According to the present invention there is provided a method for preparing a water-absorbent starch product, said method comprising: (a) forming an aqueous dispersion comprising starch, water, a free-radical initiator and an ethylenically unsaturated monomer wherein the monomer consists essentially of monomer having a boiling point of at least 100° C., and (b) simultaneously polymerizing and drying the aqueous dispersion at a temperature above 100° C. to provide a dry, water-absorbent starch product or precursor thereof. Unlike most conventional methods which typically require a plurality of steps to convert the starch and monomer to a water-absorbent starch product, the present invention permits direct conversion of the aqueous starch monomer mixture into a water-absorbent starch product.

Unrefined, starch-bearing materials, refined starches, modified and unmodified starches from a variety of starch sources (including cereal, leguminous and tuber starches) may be utilized as a starch reactant. Illustrative unrefined, starch-bearing materials include whole or defatted meals or flours obtained from starch sources such as corn, wheat, barley, oat, pea, waxy maize, arrowroot, sorghum, rice, waxy sorghum, waxy rice, soya, high amylose cereals, canna, sweet potato, potato, mixtures thereof and the like. Since the efficacy of the copolymerization reaction and the water-absorbent starch depends to a certain degree upon the reaction media starch concentration, starch-bearing materials which contain starch as the most prevalent compositional ingredient (i.e., weight exceeds next most prevalent ingredient) are best suited as a starch reactant source material. Unrefined fractions or streams obtained from the wet or dry milling of starch-bearing materials (e.g., bran, high protein starch fractions such as Merco starch, hydromilled, air-classified starches, etc.) may likewise be used. Since the reaction is conducted in an aqueous media and the desired end-product relies upon hydrophilic and water-absorbent properties, low fat or starch-bearing reactants (e.g., degummed or defatted starches) are advantageously employed. Advantageously the starch reactant source material comprises at least 50% (preferably at 65% by weight) of the total starch-bearing material weight.

Modified and unmodified refined starch-bearing materials are particularly suitable reactants for preparing the water-absorbent starch products of this invention. The starch reactant may be granular, prepasted, hydrolyzed (enzymatically or chemically), or a derivatized starch. Similarly, starch fractions (amylose fraction), dextrin, etc. may be used as a starch reactant. A wide variety of starch derivatives (e.g., starch ethers and esters, including cationic, non-ionic, anionic, amphoteric) may be utilized as the starch reactant. Illustrative derivatized starch-bearing materials include oxidized starch, starch phosphates, starch esters (the fumarates, acetates, propionates, succinates, glutamates, citrates, maleates, itaconates, etc.), alkyl ethers (e.g., ethyl, propyl, butyl, etc. starch ethers), the hydroxyalkyl ethers (e.g., hydroxyethyl starch ethers), carboxyalkyl starch ethers, nitrogen containing starch ethers (e.g., such as the cationic starches frequently used in paper and textile sizing operations), phosphonium starch ethers, starch carbamates, starch xanthates, sulfuric acid derivatives of starch, mixtures thereof and the like.

A variety of unsaturated monomers containing water-absorbtive substituents or precursors thereof may be used to prepare the starch polymerizates herein. The polymeric linkages formed by the monomers may be amphiphilic (i.e., contain both polar water-soluble and hydrophobic water-insoluble groups), anionic, cationic, non-ionic or mixtures thereof. Since relatively short reaction periods are used, the preferred water-soluble, ethylenically unsaturated monomers are those which contain an activating group adjacent to the ethylenic unsaturation.

Anionic monomers include ethylenically unsaturated monomers which contain acid groups or acid-salt groups or acid-salt precursors. Exemplary anionic substituents include carboxylates, oxalates, benzoates, phosphonates, maleates, malates, phthalates, succinates, sulfates, sulfonates, tartrates, fumarates, mixtures thereof and the like. Illustrative ethylenically unsaturated cationic monomers include nitrogen-containing cations such as primary, secondary, tertiary and quaternary ammonium compounds, sulfur containing cations such as sulphonium salts, halides, etc.; phosphorous containing cations such as phosphonium salts; mixtures thereof and the like. Typical nitrogen-containing cations include monomers represented by the formula:

$M'—(N^+R_aR_bR_c)X^-$ wherein M' represents an ethylenically unsaturated organo group, $R_a$, $R_b$ and $R_c$ represent at least one member selected from the group consisting of hydrogen and organo group, and X is an anion (e.g., halide, acetate, $CH_3SO_4^-$, $C_2H_5SO_4^-$, etc.), hydroxyalkyl, aralkyl, cycloalkyl groups as well as cyclic and heterocyclic groups divalently bonded to the nitrogen atom (e.g., $R_a$ and $R_b$ form a cyclic structure). Advantageously such nitrogen-containing ethylenically unsaturated cationic monomers are the water-soluble, monomeric salts such as the lower alkyls of 1–5 carbon atoms (e.g., ethyl, methyl, propyl); polyoxyalkylene (e.g., polyoxyethylene polypropylene, mixtures thereof and the like; alkoxy (e.g., methoxy, ethoxy, propoxy, etc.); hydroxyalkyl and polyhydroxyalkyl (e.g., hydroxyethyl, hydroxypropyl, dihydroxypropyl, dihydroxybutyl); heterocyclic amines (e.g., morpholine); amines and amides bearing monoorganics; mixtures thereof and the like. The sulfur- and phosphorus-containing cationic monomers are similar to the aforementioned except either the phosphorus atom or sulfur atom replaces the nitrogen atom. Preferably such phosphorus and sulfur cations are the phosphonium and sulphonium cationic salts.

Representative anionic monomers include vinyl sulfonic acid and vinyl sulfonates (e.g., see U.S. Pat. Nos. 3,970,604 by G. Wentworth and 2,859,191 by Turnbull, etc.); allyl sulfosuccinic acid and allyl sulfosuccinates (e.g., see U.S. Pat. No. 3,219,608 by Ingleby et al.); sulfo esters and alpha-methylene carboxylic acids and salts thereof (e.g., see U.S. Pat. No. 3,024,221 by LeFevre et al.); sulfo-organic esters of fumaric and maleic acids and salts thereof (e.g., see U.S. Pat. No. 3,147,301 by Sheetz); acids and salts of sulfatoalkane acrylates and methacrylates (e.g., see U.S. Pat. Nos. 3,893,393 by Steckler and 3,711,449 by Brendley) acrylamidoalkanesulfonic acid and salts (e.g., see U.S. Pat. Nos. 4,008,293 by Maska et al., and 3,946,139 by Bleyle et al.), vinyl phosphonic acid and vinyl phosphonates; alpha, betae-thylenically unsaturated carboxylic acids, their salts (e.g., acrylic acid, methacrylic acid, ethacrylic acid, propacrylic acid, butacrylic acid, itaconic acid, monoalkyl esters of itaconic acid, crotonic acid and crotonates, fumaric acid and fumarates, etc.), mixtures thereof and the like. More detailed description of such monomers (water-attractant moieties and precursors thereof) may be found in Belgian Patent Specification 854,010 entitled "Water-Absorbent Starch Copolymerizates" by Young et al.

The ethylenically unsaturated monomer precursors may be polymerized and subsequently converted to the water-attractant form (e.g., saponification to replace the alkyl ester group with a metal salt, and such other known techniques for derivatizing organic compounds to the neutralized acid-salt form). Preferably the polymerized monomer does not require derivatization to place the copolymerized product into the water-absorbent form. This avoids the derivatization step, the possibility of contaminating the copolymerizate with salts and minerals, then washing and refining to remove such contaminants therefrom.

In a more limited aspect of the invention, monomers characterized as essentially free from the development of volatiles when copolymerized and dried at temperatures in excess of 250° C. (preferably greater than 300° C. under atmospheric drying conditions) are advantageously used to prepare the water-absorbent starches. These essentially non-volatile monomer reactants afford safer copolymerization and more economical manufacture (e.g., toxic, health, fire, EPA, recovery, reactant loss considerations, etc.). Acid-containing monomers neutralized with non-volatile bases are the preferred monomers (e.g., see U.S. Pat. No. 2,956,046 by Glavis et al.) Such monomers can be directly converted to polymeric units containing the necessary water-attractant moieties. An additional advantage arising out of the use of such monomer salts is that they are typically non-corrosive to metals and the apparatus which is used in their preparation. A particularly well suited class of ethylenic unsaturated monomers herein include acid-containing monomers which have been neutralized with metal base to provide the monomeric salts thereof. The alkali metal (e.g., Ti, K, Na, etc.) and the alkaline earth salts (e.g., Mg, Ca, Ba, etc.), especially the acrylates and/or methacrylates thereof, are particularly useful in preparing the water-absorbent starch of this invention.

The molar ratio of starch to monomer should be sufficient to impart water-absorbent properties to the copolymerized product. Although the starch to monomer molar ratio may vary considerably, it will most generally fall within the range of about 2:1 to about 1:10 and most typically from about 1:5 to about 2:3. The most suitable ratio for any specific monomer or comonomers is interrelated to the water-attractant properties and the stearic configuration the particular copolymerized monomer imparts to the water-absorbent starch product. In general, moieties of a greater polarity typically require less copolymerized monomer than those of a lesser polarity for a given water-absorbency value. A molar ratio of about 1:2 to about 1:4 is most typically employed to provide absorbent starches capable of absorbing at least 200 times the product dry weight in distilled water.

An aqueous media is used as the polymerization vehicle for the reaction. The reactants may be uniformly dispersed throughout the aqueous media as a solute or slurry form (e.g., a granular starch slurry). Dispersants (e.g., conventional polymerization wetting agents and surfactants) may be utilized to effectuate uniform dispersal for hydrophobic reactants. Sufficient water to homogeneously disperse the starch, monomer and initiator system throughout the reaction media should be used. Conventional tap water, as well as distilled or deionized water, may be used. The most appropriate level of water will primarily depend upon the manner whereby the reactants are polymerized and dried, the physical and chemical characteristics of the reactants and particularly the starch reactants. Homogeneous dispersal of the reactants throughout the aqueous media facilitates the polymerization reaction rate and uniformity of the resultant water-absorbent starch product. Since the process entails the simultaneous polymerization and drying of the reactants, it is advantageous to avoid excessive water. Excessive water can result in incomplete polymerization of the reactants and excessive drying costs. Conversely, insufficient water can result in premature polymerization as well as nonuniform dispersal and reaction of the reactants. The more viscous starches generally require more water for homogeneous dispersal than starches of a lesser viscosity. For most applications, the amount of water needed to uniformly disperse the reactants ranges from about 10% to about 90% by weight water. Extrusion, calendering, etc. processes are typically operated at the higher solids level (e.g., about 70% to 90% dry solids) while spray-drying, flash-drying, etc. processes are typically operated between about a 10% to 40% dry solids concentration. Roll-dried and polymerized products and advantageously prepared from aqueous dispersions containing from about 30% to about 70% by weight water. Aqueous media containing from about 45% to about 60% by weight water are most suitable for roll-drying polymerization operations.

The reactants are polymerized by conventional initiating means. Although conventional irradiation processes which generate free-radicals (e.g., electron-beam, X-ray, alpha-ray, gamma-ray, etc. initiation) may be utilized to effectuate the polymerization, it is advantageous to uniformly incorporate free-radical catalysts or free-radical precursors into the unpolymerized aqueous dispersion. Illustrative free-radical polymerization initiators at levels sufficient to initiate the polymerization (e.g., about 0.01% to about 20% on a total monomer weight basis) include the organic and inorganic peroxides (e.g., hydrogen peroxide, benzoyl peroxide, tertiarybutyl hydroperoxide, di-isopropyl benzene hydroperoxide, cumene hydroperoxide, caproyl peroxide, methyl ethyl ketone peroxide, etc.), persulfates (e.g, ammonium, potassium or sodium persulfates, etc.) or redox systems such as persulfates or hydrogen peroxide with reducing agents such as sodium bisulfites, sulfites, sulfoxylates, thiosulfates, hydrazine, etc.); azo initiators (e.g., tertiary aliphatic azo compounds which undergo homolytic dissociation) such as azo di-isobutyronitrile, phenylazotriphenylmethane, 1,1'-azodicyclohexanecarbonitrile, 1,1-dimethylazoethane; diazoamino compounds (e.g., 3,3-di-methyl-1-phenyl-triazene and arylidiazo thioethers), certain aromatic ketones (e.g., benzoin methyl ether, benzophenone and its derivatives), chlorinated aromatics, mixtures thereof and other free-radical type initiators.

Conventional promoters at concentrations conventionally used to reduce the free-radical generation and polymerization temperatures to ambient conditions can be adapted to the process provided they are properly introduced into the process to permit concurrent polymerization and drying of the reactants. The redox systems are illustrative means which afford free-radical catalysis at ambient temperatures. By reducing the proportion of promoter to initiator, the thermal initiating temperature of the catalyst system will generally inversely increase. Thus, the promoter to initiator ratio may be partially used to control the polymerization temperature.

The polymerization catalyst system is tailored to fulfill the particular process conditions employed to dry and polymerize the aqueous dispersion. Catalyst systems requiring relatively high temperature for activation may be suitably adapted to those processes requiring a relatively high temperature to form the aqueous dispersion without initiation, but will become thermally initiated when exposed to the more elevated temperatures employed to dry and polymerize the reactants (thermally staged extrusion processes). Promotor elimination or reduction to a level substantially below those levels conventionally used to initiate ambient temperature polymerization reactions can be effectively tailored to the free-radical generation thermal requirements for the particular drying and polymerization requirements of any given process. In the absence or promoter, initiators such as the organic and inorganic peroxides and persulfates, etc., will typically require temperatures in excess of 60° C. (e.g., at pragmatic initiator concentrations such as <10% of the monomer weight) to generate free-radicals. The free-radical initiation temperature for peroxides per se are typically effectuated at temperatures above 100° C. to about 300° C. or higher, but usually less than 200° C. (e.g., <150° C. as disclosed in U.S. Pat. No. 3,366,605 by Seiner and patents cited therein). In the absence of promoter, appreciable free-radical initiation with the persulfate initiators occurs at temperatures of about 70° C. and higher, and especially at temperatures between about 75° C. to about 95° C.

The initiator concentration has an effect upon the quantum of free-radicals generated at any given temperature. Irrespective of the type of initiator employed, a sufficient initiator concentration to effectuate polymerization under the process drying conditions is provided to the polymerization reaction site. The actual initiator concentration necessary to achieve this result depends upon the reaction temperature, the reaction time and the free-radical initiating temperature of the initiator. Accordingly, the initiator level may vary considerably (e.g., from about 0.1% to about 10% of the monomer weight). Peroxide initiator concentrations are typically greater (e.g., 1–10%) than persulfate initiated systems (e.g., 0.03–3%). In most operations, the initiator concentration may range from about a 2 to about a 6 fold increase over the most effective conventional ambient temperature redox catalyst systems (e.g., such conventional systems range from about 1 to about 3% for promoted peroxide initiators and about 0.25% to about 0.5% monomer weight for promoted persulfated initiators).

The persulfate initiators (without promoters), especially the ammonium persulfate and the alkali metal persulfates (e.g., potassium, lithium, sodium, etc.) are particularly unique in their ability to serve as catalysts for the polymerization and drying of the present water-absorbent starches. Free-radical generation with such persulfate initiators can broadly range at processing temperatures from about 65° C. for a relatively long contact time (e.g., 15 minutes) to about 320° C. for a short contact time (e.g., 1–2 seconds, as typically encountered in a spray-drying process). In roll-drying operations the persulfate concentration (monomer weight basis) will generally fall within the range of about 0.03% to about 2.0%, and preferably between about 0.05% to about 1.5% with a persulfate concentration ranging from about 0.1% to about 0.8% being most preferred.

Alternatively, premature polymerization (e.g., without concomitant drying) can be effectively avoided by controlling the stage at which the polymerization initiator is introduced into the aqueous dispersion. In processes which, prior to drying, relay upon relatively high temperatures (e.g., > 60° C.) for several seconds or more to achieve homogeneous reactant dispersal, initiator addition may be delayed until immediately before or concurrently with the drying step. Conversely, in those processes wherein homogeneous dispersal can be effectively accomplished without exposing the reactants to polymerization conditions before drying, the polymerized catalyst system can be appropriately selected to generate free-radicals when the reactants are exposed to the elevated temperature of the drying step. In general, processes which rely upon relatively high temperature (e.g., > 70° C.) at a high solids level (e.g., less than 40% water) are most suitably conducted under the delayed initiator incorporation technique whereas the low temperature (e.g., > 50° C.) and low aqueous dispersion solids processes (e.g., spray-drying, roll-drying, etc. at 50% or more water) are most suitably conducted in the presence of a thermally initiated polymerization catalyst system.

The reactants are simultaneously polymerized and dried to yield a water-absorbent starch product. The polymerization rate will depend upon the reactivity of the reactants, reactant concentration, the efficacy of the catalyst system, the reaction temperature and the polymerization time. The most appropriate thermal conditions depend upon the particular apparatus used to simultaneously dry and polymerize the homogeneous dispersion. Illustrative processes for simultaneously polymerizing and drying the homogeneous dispersion include extrusion, heat-exchanging, votating, calendering, spray-drying, flash-drying and drum-drying processes, etc. Usually the simultaneous drying and polymerization temperature will range between 100° C.–250° C. with definitive product and processing advantage being accomplished at less than 200° C. In comparison to conventional, reaction vessel polymerization processes which typically require more than 10 minutes, the present polymerization is usually completed within three minutes. Processes capable of drying and polymerizing the reactants within about 1 to about 90 seconds time interval (advantageously less than 60 seconds) at reaction temperature ranging from about 110° C. to about 160° C. are best suited for the manufacture of a high quality water-absorbent starch product. Although the polymerized and dried product may be post-dried, the drying and polymerization conditions are most suitably conducted to provide a water-absorbent starch product containing less than 25% by weight water.

In a more limited embodiment of the invention, the water-absorbent starch products are prepared via roll-drying processes. Single drum or multiple drum-driers (e.g., double drums, twin drums, etc.) are well suited for this manufacture. The temperature and reaction time is appropriately maintained so as to provide the water-absorbent starch product. The polymerization and drying conditions are effectively controlled by the operational drum speed (i.e., contact time) and drum temperature. The drum surface temperature and contact time are desirably maintained at a level sufficient to reduce the water content of the water-absorbent starch product to less than 20% and preferably to less than 15% by weight water. The drum surface temperature is most typically maintained from about 100° C. to about 180° C. Contact time of the reactants upon the drum surface can vary considerably (e.g., about 1–90 seconds) with a contact time between about 5 to about 60 seconds being generally applicable to most drum-drying operations. More effective manufacture and improved product functionality is accomplished when the surface temperature of the drum-drier ranges from about 120° C. to about 160° C. with a contact time ranging from about 25 to about 50 seconds and preferably between about 120°–140° C. and a contact from about 30 to about 40 seconds. Excessive drum speed or excessively low temperatures may result in incomplete polymerization whereas excessively slow speeds at the more elevated temperatures can char the product.

The homogeneous dispersion application to the roll-drier is at a rate sufficient to permit its drying and polymerization into a water-absorbent starch product or precursor thereof. Excessively thick films or non-uniform application can result in incomplete or non-uniform polymerization and drying of the product. Conversely, too thin of an application can result in product charring (especially at elevated temperatures) or inefficient production. In general, the roll-process typically provides a dried film of a thickness ranging from about 1 mil. to about 50 mils with about 5 to about 25 mils film thickness being most typical. Water-absorbency and processing efficiency are best optimized under roll-drying conditions which provide a roll-dried film thickness of about 10 to about 15 mils.

In order to enhance or accelerate the polymerization, two or more comonomers may be copolymerized. Monomers free from water-attractant groups or water-attractant precursor may be used for this purpose in minor amounts. Although water-insoluble comonomers may be utilized (e.g., placed in homogeneous dispersion by water-miscible organic solvent systems or surfactants), the water-soluble comonomers are best suited. The hydroxyalkyl esters and $C_1$-$C_2$ alkyl esters of alpha, beta-ethylenically unsaturated acids; the alpha, beta-ethylenically unsaturated amides; vinyl esters, vinyl alcohol and vinyl ethers; vinyl pyrrolidone, mixtures thereof and the like are illustrative comonomers which are essentially free from effective water-absorbent moieties, but which may be copolymerized with the water-attractant monomers mentioned hereinbefore. Further information pertaining to such other comonomers may be found in Belgian Patent Specification No. 854,010 by Yound et al. mentioned above. Efficacy of the water-absorbent starch product directly correlates to the amount of polymerized water-attractant monomers in the product. Likewise, the process is simplified by drying and polymerizing in situ monomer and/or comonomer combinations which impart the necessary water-absorbency to the product without requiring additional processing to provide the water-absorbent product. Accordingly, product and process performance are improved by polymerizing aqueous dispersions containing a water-attractant monomer to other comonomer (including both precursors and non-water attractant monomers) molar ratio of more than 2:1 with further improvements being obtained when the molar ratio is at least 3:1. The non-volatile salts of ethylenically unsaturated acid-containing monomers in an amount containing at least 85% and preferably more than 90% the total monomer weight are especially well suited for practicing the invention.

Unlike water-absorbent starch products derived from the polyacrylonitrile starch grafts, the present water-absorbent starches contain unpolymerized monomer residues having a boiling point of at least 100° C. (analytically detectable residues). Such residues arise because of incomplete monomer polymerization (e.g., high monomer concentration, short contact time, the initiation system, etc.). The monomer residue will not adversely affect water-absorbency provided the product contains a sufficient level of copolymerized monomer. The free monomer residue in the present water-absorbent starch product generally falls within about 0.01% to about 5% of the dry product weight range with residue levels of about 0.05% to less than 3% being most typical. In drum-drying processes, the residue monomer content is advantageously maintained at less than 1% (e.g., 0.1–1%) and preferably below 0.05% with about 0.15% to about 0.30% by weight residue being most typical.

The polymerized ethylenically unsaturated monomer portion of the present water-absorbent starches may consist essentially of repeating units of the polymerized water-attractant or salt groups as opposed to about 67% maximum for the acrylonitrile grafted copolymers. If two or more comonomers are polymerized, the polymerized monomeric portion of the present water-absorbent starch will be irregular as opposed to the essential regular sequence of polymerized monomeric units present in water-absorbent starch products derived from acrylonitrile graft copolymers. This difference is believed to arise because of the randomness of copolymerization reaction herein (e.g., comonomer reactivity kinetics) in contrast to the acrylonitrile saponification which essentially yields a uniform chemical conversion of sequential repeating units. Since the present process does not necessitate the use of heavy metal catalysts for polymerization initiation, the water-absorbent starches of this invention can be provided in a form essentially free from heavy metal contaminants such as ceric ions.

The drum-dried product (without any further processing) will readily disperse into aqueous systems and absorb large amounts of water. If desired, the drum-dried sheets or films may be ground to a suitable particle size for purposes of facilitating its water-dispersibility and providing a means for more accurately controlling the amount of water-absorbent product incorporated into the aqueous systems. Particles having a particle size ranging from about 25 to about 1,000 microns and preferably between about 50 to about 200 microns are generally acceptable for this purpose. In the absence of shear, the water-absorbent particles uniformly hydrate throughout the entire mass (without concomitant fish eyes) to provide discrete, macroscopic sac-like masses of highly water-swollen particles. The discrete, macroscopic character of these highly water-swollen particles can be disintegrated by mechanical shear to typically provide an aqueous mass of an intermediate viscosity (e.g., greater than about 100 cps to less than 5,000 cps at 2% dry solids concentration and 25° C.). In contrast thereto, drum-dried physical blends of polypotassium acrylate and starch at an equivalent concentration typically provide low viscosity aqueous products whereas the polyacrylonitrile-starch grafts typically yield a highly viscous system (e.g., greater than 25,000 cps). The intermediate viscosity and high water-absorbency characteristics of the present water-absorbent starches enhance their utility for coating and fabricating applications.

The water-absorbent starches herein characteristically have a water-absorbency (WA) of at least 10 and most generally at least 50. Since the drum-dried products may be directly prepared from water-attractant monomers without necessitating any further chemical modification or hydrolysis, contaminants need not be removed therefrom by cumbersome and costly refining steps. Advantageously the monomer and starch reactants (including the type and proportions thereof) are selectively copolymerized under conditions which yield a water-absorbency value of at least 150. The unrefined, copolymerized metal salts of alpha, beta-ethylenically unsaturated acid monomers and particularly the alkali and alkaline earth acrylates or methacrylates, characteristically provide a water-absorbency of at least 200 to about 600 and higher. Preferably the products have a water-absorbency of at least 300.

Due to the processing simplicity and high water-absorbency of the crude or unrefined product provided by this invention, the product purification is generally unnecessary for products directly manufactured from the water-attractant salt monomers. Similar to the hydrolyzed polyacrylonitrile graft starch copolymers, the hydrated and reconstituted water-absorbent starches herein are ineffective and form gelled masses under highly acidic conditions (e.g., pH 3.0 or less). If the starch product is obtained from precursors, this characteristic can be effectively used to refine the water-absorbent starch product. Refining will increase the water-absorbency of the starch product to the extent that the non-functional impurities are removed therefrom.

Water-absorbent starches of more than 75% water-soluble salts of ethylenically unsaturated acids tend to yield different products when adjusted to pH 2.5 than either the drum-dried physical blends of the corresponding polymer and starch or the water-absorbent starches derived from hydrolyzed polyacrylonitrile-starch grafts. The latter two upon addition of concentrated aqueous methanol (e.g., a 5:1 - methanol to water volume ratio) typically form precipitates (e.g., at a 2% product concentration on a d.s. basis, pH 2.5 and 20° C.), whereas the former products form gels which when dried will upon subsequent aqueous reconstitution have water-absorbent properties. In contrast to the hydrolyzed polyacrylonitrile starch grafts which typically do not provide a starch fraction soluble in concentrated aqueous methanol, a substantial portion of the present products are soluble therein (e.g., greater than 5% and typically between about 10–20%).

Unless stated otherwise, the water-absorbency values were determined as follows. A dry water-absorbent product is ground through a 16 mesh sieve (#18 U.S. series) and a 0.25 gram portion (dry substance weight basis) thereof is sifted onto the surface of 500 g distilled water (pH 7.0 at 25° C.) contained in a 600 ml. glass beaker. The 0.25 gram portion is then allowed to quiescently hydrate and reconstitute into the water for five (5) minutes at 25° C. The hydrated and reconstituted water-absorbent starch product is then gently poured through the center of a 20.3 cm diameter sieve (#40 mesh, U.S. series), positioned above a tared filtrate collector at 35° from horizontal. After permitting the filtrate to drain for 10 minutes, the collected filtrate is weighed and the water-absorbency (WA) is determined by the following equation:

$$500 \text{ gm - filtrate weight (gms)}/0.25 \text{ gm} = WA$$

The following examples are illustrative of the invention.

EXAMPLE I

The water-absorbent starch was prepared from the following ingredients:

| INGREDIENTS | PARTS BY WEIGHT |
| --- | --- |
| Pearl Starch (d.s.) | 100.0 |
| Acrylic Acid | 150.0 |
| Potassium Hydroxide | 122.0 |
| Ammonium Persulfate | 1.0 |
| Water (total) | 565.0 |

A 33% potassium hydroxide solution (122 g of potassium hydroxide, 248 g of distilled water) was prepared. To a chilled metal beaker, 150 g of glacial acrylic acid was admixed with 301 g of tap water. The aqueous acrylic solution was then slowly neutralized to a pH 7.0 with the potassium hydroxide solution while maintaining its temperature below 50° C. The pearl starch (118 g - as is basis) was then added and admixed into the resultant potassium acrylate solution to provide a starch slurry. To the pearl starch slurry (pH 7.0 at 38° C.) there was then added the ammonium persulfate (20% by weight aqueous solution). The resultant homogeneous aqueous dispersion slurry was directly fed to a Blaw-Knox Food & Chemical Equipment, Inc. laboratory double-drum dryer, pre-set at a 35–40 mm clearance between drums and preheated to a no-load drum surface temperature of 132° C.–138° C. to produce a 0.254mm thick, friable film of water-absorbent starch product. The resultant product had a water-absorbency of 450 (i.e., absorbs 450 times its weight in water). The residual monomer content weight (i.e., unpolymerized monomer-dry product weight basis) was 0.4%.

EXAMPLE II

A water-absorbent product was prepared by modifying the Example I process (as indicated) employing the following ingredients:

| INGREDIENTS | WEIGHT (gms) |
| --- | --- |
| Acid-thinned, granular waxy maize starch[1] | 198.0 |
| Tap water (pH 9.0) | 620.0 |
| Acrylic Acid | 140.0 |
| Potassium Hydroxide | 120.0 |
| Acrylamide | 35.0 |
| Ammonium persulfate | 0.9 |

1 - STA-TAPE 100 - manufactured by the A. E. Staley Manufacturing Company - A low viscosity, acid-thinned, granular waxy maize starch (100% amylopectin) typically characterized as having a Brookfield viscosity of about 500 cps (#2 spindle, 20 rpm, 150° C. at a dry solids of 40–45%) and a D.E. of less than 1%.

The starch and the water were heated at 95° C. for 15 minutes. The starch paste was cooled to 35° C. and the acrylic acid was added. The vessel containing the starch paste solution was then placed into an ice bath and the potassium hydroxide slowly added until pH 7.0 is reached. After the caustic addition was completed, the acrylamide was added. The resultant aqueous dispersion by hand refractometer indicated 39% solids. A sample of the water-absorbent starch was reconstituted and rehydrated in distilled water (2% d.s. water-absorbent starch) per the water absorbing procedure. Water absorbency of the product was 296.

EXAMPLE III

In accordance with the general methodology of Example I, a series of water-absorbent starch products were prepared. The ingredients, processing conditions and water-absorbency of the products are reported in Table 1. Tap water was used in all the Runs except demineralized water was used in Run 9. The homogeneous aqueous dispersion contained 40% dry solids, drum contact time was 34 seconds with the operational drum surface temperature employed in preparing the products indicated in the 121° C., 135° C., and 150° C. columns under the water-absorbency heading. As evident from Table 1, various starches and starch bearing materials may be used. By adding supplemental starch to corn bran, the water-absorbency properties of the corn bran were significantly improved (e.g., see Runs 12 and 13). As illustrated by Runs 14–16, the drum-dried aqueous dispersions need not be completely neutralized in order to provide polymerized starch products having good water-absorbent properties. Residue unpolymerized monomer for Runs 14, 15 and 16 at 121° C. and 135° C. were respectively 0.5% and 0.3%, 0.6% and 0.4%, and 0.4% and 0.4%. Granular starches were employed in all Runs except for Run 4 which used a pasted starch.

TABLE 1

| Run No. | Starch | Starch/Monomer Mole Ratio | Monomer AA[6] % | Monomer AM[7] % | Initiator[8] % Monomer Wt. | Alkali Neutralization Type | pH | Water-Absorbency 121° C. | Water-Absorbency 135° C. | Water-Absorbency 150° C. |
|---|---|---|---|---|---|---|---|---|---|---|
| 3 | Cationic Potato Starch[2] | 1:2 | 80 | 20 | 0.5 | K+ | 7.0 | 97 | 156 | — |
| 4 | STA-TAPE 100[1] | 1:2 | 95 | 5 | 0.5 | K+ | 7.0 | 340 | 313 | — |
| 5 | Pea Starch[3] | 1:2 | 95 | 5 | 0.5 | K+ | 7.0 | 200 | 193 | — |
| 6 | Pearl Starch (corn) | 1:2 | 95 | 5 | 0.5 | Na+ | 7.0 | 142 | 77 | 38 |
| 7 | Wheat Starch | 1:3.4 | 100 | — | 0.7 | K+ | 7.0 | 350 | 289 | — |
| 8 | Pea Starch[3] | 1:3.4 | 100 | — | 0.7 | K+ | 7.0 | — | 256 | — |
| 9 | Pearl Starch (corn) | 1:3.4 | 100 | — | 0.7 | K+ | 7.0 | 411 | 357 | — |
| 10 | Corn Meal | 1:3.4 | 100 | — | 0.7 | K+ | 7.0 | 374 | — | — |
| 11 | Whole Wheat | 1:3.4 | 100 | — | 0.7 | K+ | 7.0 | 343 | 316 | — |
| 12 | Corn Bran[4] | 1:3.4 | 100 | — | 0.7 | K+ | 7.0 | 17 | — | — |
| 13 | Pearl Corn/Corn Bran[5] | 1:3.4 | 100 | — | 0.7 | K+ | 7.0 | 343 | 300 | — |
| 14 | Pearl Starch (corn) | 1:3.4 | 100 | — | 0.7 | K+ | 5.5 | 304 | 345 | — |
| 15 | Pearl Starch (corn) | 1:3.4 | 100 | — | 0.7 | K+ | 6.0 | 409 | 375 | — |
| 16 | Pearl Starch (corn) | 1:3.4 | 100 | — | 0.7 | K+ | 6.5 | 352 | 349 | — |

[1] - Supra
[2] - STA-LOK 400, manufactured and distributed by A. E. Staley Manufacturing Company, Decatur, Ilinois
[3] - Granular Pea Starch of about a 35% amylose content.
[4] - Corn Bran comprised of 10% by weight starch and 20% cellulose
[5] - 90% pearl/10% corn bran (weight)
[6] - acrylic acid
[7] - acrylamide
[8] - Percent ammonium persulfate based on total monomer weight

EXAMPLE IV

In this example a series of comparative studies were conducted upon different water-absorbent starch products. The study illustrates the physical and compositional differences between the drum-dried and polymerized starch-potassium acrylate products herein, drum-dried physical blends of starch and polyacrylates, and hydrolyzed polyacrylonitrile starch grafts. The data is recorded in Tables 2 and 3. Pearl starch (corn) alone without any added monomer or polymer was used in Run 22.

In Run No. 19, 0.7% by weight potassium persulfate initiator (monomer wt.) was used whereas Run Nos. 17, 18 and 20–24 contained 0.7% by weight ammonium persulfate initiator. The drum speed was 54 Secs./revolution (contact time 34 seconds) at a pH 7.0 with a 121° C. surface drum temperature for Runs 17 and 24, and 135° C. for Runs 18–23. In Runs 20, 21 and 24, a polyacrylic acid polymer (Rohm & Haas A-3) was neutralized before drum drying to pH 7.0 with potassium hydroxide. Run 25 is a water-absorbent corn starch product obtained from a hydrolyzed polyacrylonitrile graft starch polymer prepared in accordance with U.S. Pat. No. 3,977,484.

The stock solution viscosity determinations in Table 2 were made by sifting the water-absorbent starch products through a 16 mesh sieve into distilled water, shearing for 1 minute with a Waring Blendor (1043 model) at the low speed. The Table 2 viscosity values were determined with a Brookfield viscometer RVT (at 100 rpm and 25° C.) at the designated concentrations and pH's.

The blended samples were then adjusted to a pH 2.5 with concentrated hydrochloric acid. An aliquot of the pH 2.5 adjusted aqueous media was then removed under sufficient agitation to insure its homogeneity. The analysis of each pH 2.5 stock solution is tabulated in Table 2. The remaining portion of the homogeneous samples were then individually dispersed at pH 2.5 into sufficient methanol to provide a final water/methanol weight ratio of 1:5. Each sample was cooled to 25° C., centrifuged at 190 g's for 5 minutes with the supernatant being decanted therefrom for analysis of the water/methanol solubles. Each centrifugate (a precipitate in Runs 20–22 and 24–25 and gel in Runs 17–19 and 23) was then redispersed in 50 ml. methanol and the centrifugate and supernatant decantation steps were repeated as above. The two centrifugates and two supernatants for each sample were analyzed for total water/methanol solubles and water/methanol insolubles, which are reported in Table 3.

As illustrated by the above data, the drum-dried potassium polyacrylate-starch blends exhibited poor water-absorbency properties whereas the starch-monomer polymerizates are excellent water-absorbents. Table 3 illustrates that essentially all of the starch molecules have been chemically modified or grafted with the polymerized monomer (including both the supernatant and centrifugate portions). The water-alcohol supernatant for Runs 17–19 and 23 significantly differ from Runs 20–22 and 24–25. As evidenced by the Table 3 data, the drum-dried polymer-starch mixtures were easily separated into starch and polymer fractions. The water-absorbent products of Runs 17–19 and 23 yielded a gelled mass whereas both the drum-dried physical blends and the hydrolyzed polyacrylonitrile starch graft products of U.S. Pat. No. 3,977,484 precipitated. The fractionation of Runs 20–21 and 24 shows that the drum-drying of starch-polymer blends does not impart any appreciable water-absorbency thereto, whereas the inherent water-absorbency properties were retained in the water-absorbent products of Runs 17–19, 23 and 25. The data provides evidence that the drum-dried starch-monomer mixtures herein are interpolymerized to starch-acrylate graft copolymers. At the 35% AM – 65% AA level, the products herein form precipitates similar to the Run 25 product.

Employing a 1% sheared solution (sample weight) heated at 95° C. for 10 minutes, cooled to 25° C. and a 75 gram aliquot thereof, turbidity tests have been determined on a Brinkman PC-600 colorimeter equipped with a 880 nanometer filter and automatic chart recorder. In the tests, the pH is gradually and continually reduced from the initial alkaline pH of the sheared solution to a final pH of 1.5 (1.0 pH unit/Min). The sheared solutions of the polymerized starch-monomer and hydrolyzed starch graft (i.e., Run 25) typically exhibit a significant increase in turbidity as the pH approaches 3.5 with a maximum turbidity being obtained at a pH 2.5. The sheared solutions of the physical blends exhibits turbidity at alkaline pH's with no turbidity increase being recorded at the acidic pH's. The hydrolyzed polyacrylonitriles typically show a substantial reduction in turbidity below a pH of 2.5 (e.g., pH 2.0). In contrast, the drum-dried polymerizate of Runs 17–19 and 23 (as well as other unreported products) evince little, if any, fluctuation in turbidity within the pH 1.5–2.5 range. It is believed these turbidity results provide further evidence that the present products are grafted starch copolymers.

The water-absorbency values for each of the products were: 220 for Run 17; 373 for Run 18; 345 for Run 19; 0 for Runs 20, 21, 22 and 24, 300 for Run 23 and 500 for Run 25.

essentially of monomer having a boiling point of at least 100° C.; and b. simultaneously polymerizing and drying the aqueous dispersion at a temperature above 100° C. to provide a dry, water-absorbent starch product or precursor thereof.

2. The method according to claim 1 wherein at least a major weight portion of the polymerized monomer comprises the salt of alpha, beta-ethylenically unsaturated acid.

3. The method according to claim 1 wherein the starch to monomer molar ratios ranges from about 2:3 to about 1:5 at least 80% of the monomer weight comprises an alkali metal salt of an alpha, beta-ethylenically unsaturated acid, and the dispersion is simultaneously dried and polymerized at a temperature ranging from about 120° C. to about 140° C.

4. The method according to claim 2 wherein the free-radical initiator comprises a persulfate initiator.

5. The method according to claim 1 wherein the aqueous dispersion contains from about 30% to about 70% by weight water, the simultaneous polymerization and drying of the aqueous dispersion is effectuated upon the surface of at least one roller at a temperature ranging from about 100° C. to about 200° C.

TABLE 2

| | | Components | | | Stock Soln. | | | at pH 2.5 % Starch |
|---|---|---|---|---|---|---|---|---|
| | Starch: | Starch: Polypotassium | Hydrolyzed | Stock Solution After Shear | | | |
| Run No. | Starch | Potassium Acrylate Monomer Mole Ratio | Acrylate Mole Ratio | Polyacrylo-Nitrile Graft | Solids (%) | Viscosity (CPS) | pH | Actual Theoretical |
| 17 | Pearl | 3:10 | — | — | 2.2 | 620 | 9.0 | — |
| 18 | Pearl | 3:10 | — | — | 2.34 | 610 | 8.8 | 25.8/25 |
| 19 | Pearl | 3:10 | — | — | 2.1 | 670 | 9.1 | 22/25 |
| 20 | Pearl | — | 1:3 | — | 2.54 | 43 | 7.7 | 29/28 |
| 21 | Pearl | — | 1:3 | — | 2.57 | 42 | 7.7 | 31/28 |
| 22 | Pearl | — | — | — | 1.1 | 10 | — | — |
| 23 | Waxy Maize | 3:10 | — | — | 2.5 | 760 | 9.0 | 24/25 |
| 24 | Waxy Maize | — | 1:3 | — | 2.5 | 53 | 7.7 | 27.7/28 |
| 25 | Corn | — | — | 100% | 0.8 | >10,000 | 7.4 | 33 |

TABLE 3

| | | Precipitate After Addition to Methanol | | | Water/Methanol Solubles | | | |
|---|---|---|---|---|---|---|---|---|
| Run No. | Product | Appearance | Recovered Solids/ Theor. Starch | Starch Content (%) | Recovered Solids/ Theoretical | Starch Content (%) | Material Balance | Aqueous Alkali Response |
| 17 | polymerized starch-potassium acrylate | grey gel | 1.14/0.95 | — | 2.4/2.85 | 14.3 | 97 | Ppt. swells |
| 18 | " | grey gel | 1.83/2.44 | 43.7 | 7.83/7.32 | 17.8 | 99 | Ppt. swells |
| 19 | " | grey gel | 2.0/1.6 | 47.2 | 4.2/4.7 | 10.8 | 98 | Ppt. swells |
| 20 | starch-poly (potassium acrylate) blend | white flake | 2.7/2.85 | 92.3 | 7.32/7.34 | 3.7 | 99 | no effect |
| 21 | " | white flake | 2.83/2.99 | 87.8 | 7.49/7.69 | 3.9 | 97 | no effect |
| 22 | Pearl (corn) | white flake | 3.48/3.41 | 94.3 | — | — | 102 | no effect |
| 23 | polymerized starch-potassium acrylate | grey gel | — | 47.3 | — | 10.4 | — | Ppt. swells |
| 24 | starch-potassium acrylate polymer blend | white flake | 2.27/2.83 | 86.6 | 7.8/7.32 | 6.7 | 99 | no effect |
| 25 | hydrolyzed graft copolymer | brown solid | 2.2 | 40.6 | 0.8 | 0.0 | 92 | Ppt. swells |

Since many embodiments of this invention may be made and since many changes may be made in the embodiments described, the foregoing is interpreted as illustrative and the invention is defined by the claim appended hereafter.

What is claimed is:

1. A method for preparing a water-absorbent starch product, said method comprising:
   a. forming an aqueous dispersion comprising starch, water, free-radical initiator and ethylenically unsaturated monomer wherein the monomer consists 6. The method according to claim 5 wherein the aqueous dispersion comprises from about 45% to about 60% by weight water, the monomer comprises at least 95% by weight of a water-soluble metal salt of an ethylenically unsaturated acid monomer and the starch to monomer ratio ranges from about 2:1 to about 1:10.

7. The method according to claim 6 wherein the free-radical initiator consists essentially of a persulfate initiator and the monomer is the alkali or alkaline earth salt of at least one member selected from the group consisting of acrylic and methacrylic acid.

8. The method according to claim 7 wherein the aqueous dispersion is simultaneously dried and polymerized upon the surface of at least one roller at a temperature ranging from about 110° C. to about 150° C.

9. The method according to claim 7 wherein the polymerized monomer consists essentially of at least one monomer selected from the group consisting of potassium acrylate and potassium methacrylate.

10. The method according to claim 9 wherein the simultaneous polymerization and drying of the aqueous dispersion is effectuated by a drum-drying process.

11. The water-absorbent starch product prepared in accordance with the method of claim 1.

12. The water-absorbent product prepared in accordance with the method of claim 3.

13. The water-absorbent starch product prepared in accordance with the method of claim 6.

14. The water-absorbent starch product prepared in accordance with the method of claim 10.

* * * * *

UNITED STATES PATENT AND TRADEMARK OFFICE
CERTIFICATE OF CORRECTION

PATENT NO. : 4,155,888

DATED : May 22, 1979

INVENTOR(S) : Robert A. Mooth

Page 1 of 2

It is certified that error appears in the above-identified patent and that said Letters Patent are hereby corrected as shown below:

Column 3, line 56, for "$M'-(N'^+R_a R_b R_c)X^-$" read ---$M'-\overset{+}{N}R_a R_b R_c)X^-$---

Column 4, bridging lines 1 and 2, for "(polyoxyethylene polypropylene" read ---(polyoxyethylene and polypropylene)---

Column 5, line 4, for "Ti" read ---Li---

Column 6, line 55, for "or" read ---of---

Column 7, line 30, for "15 minutes" read ---5 minutes---

Column 7, line 43, for "relay" read ---rely---

Column 7, line 58 for " >50°C." read --- <50°C.---

Column 9, line 19, for "Yound et al." read ---Young et al.---

Column 11, line 39, for "500 gm - filtrate weight (gms)/0.25 gm = WA" read ---$\dfrac{500 \text{ gm - filtrate weight(gms)}}{0.25 \text{ gm}} = WA$---

Column 16, line 12, for "ratios" read ---ratio---

Column 17, line 6, for "monomer ratio" read ---monomer mole ratio---

UNITED STATES PATENT AND TRADEMARK OFFICE
CERTIFICATE OF CORRECTION

PATENT NO. : 4,155,888
DATED : May 22, 1979
INVENTOR(S) : Robert A. Mooth

It is certified that error appears in the above-identified patent and that said Letters Patent are hereby corrected as shown below:

Column 4, line 2, for "polypropylene" read ---polyoxypropylene---
Column 16, line 13, for "about 1:5 at least" read ---about 1:5, at least---

Signed and Sealed this

Second Day of October 1979

[SEAL]

Attest:

RUTH C. MASON
Attesting Officer

LUTRELLE F. PARKER
Acting Commissioner of Patents and Trademarks